United States Patent [19]

Johnson et al.

[11] Patent Number: 4,593,148

[45] Date of Patent: Jun. 3, 1986

[54] PROCESS FOR REMOVAL OF ARSINE IMPURITIES FROM GASES CONTAINING ARSINE AND HYDROGEN SULFIDE

[75] Inventors: Marvin M. Johnson; Gerhard P. Nowack, both of Bartlesville, Okla.

[73] Assignee: Phillips Petroleum Company, Bartlesville, Okla.

[21] Appl. No.: 715,549

[22] Filed: Mar. 25, 1985

[51] Int. Cl.$^4$ .......................... C07C 7/12; C01B 3/00; C10G 65/06; C10G 61/06

[52] U.S. Cl. .................................... 585/823; 585/845; 585/868; 208/49; 208/97; 208/212; 208/253; 423/210

[58] Field of Search ....................... 585/823, 845, 868; 208/253, 88, 211, 97, 212, 49; 423/210

[56] References Cited

U.S. PATENT DOCUMENTS

| | | | |
|---|---|---|---|
| 2,511,289 | 6/1950 | Morrell et al. | 252/447 |
| 2,781,297 | 2/1957 | Appell | 196/44 |
| 3,660,276 | 5/1972 | Lacey | 208/212 |
| 3,812,652 | 5/1974 | Carr et al. | 55/68 |
| 4,048,387 | 9/1977 | Lahme et al. | 429/50 |
| 4,088,734 | 5/1978 | Gadelle et al. | 423/210 M |
| 4,300,997 | 11/1981 | Meguerian et al. | 208/120 |
| 4,300,999 | 11/1981 | Davies et al. | 208/212 |
| 4,462,896 | 7/1984 | Kitagawa et al. | 585/823 |

OTHER PUBLICATIONS

"Comprehensive Inorganic Chemistry", vol. 3, by J. C. Bailar et al., Pergamon Press, 1973, pp. 219, 232.
"Girdler Catalysts", Girdler Chemical, Inc., 1977, pp. 8, 17 and 20.

Primary Examiner—Andrew H. Metz
Assistant Examiner—Chung K. Pak
Attorney, Agent, or Firm—K. K. Brandes

[57] ABSTRACT

Arsines are removed from gaseous stream, e.g., hydrocarbon or inert gas streams, comprising arsine impurities and also hydrogen sulfide, by contacting these gas streams with a sorbent material comprising copper oxide and zinc oxide. Preferably, the sorbent material is prepared by coprecipitating of hydroxides of copper and zinc and subsequent heating the hydroxides so as to convert the hydroxides to CuO and ZnO. Optionally, aluminum oxide is also present in the sorbent material.

25 Claims, No Drawings

PROCESS FOR REMOVAL OF ARSINE IMPURITIES FROM GASES CONTAINING ARSINE AND HYDROGEN SULFIDE

This invention relates to the treatment of various gases for the removal of arsenic impurities. In one embodiment, the invention relates to methods of removing arsenic impurities from petroleum fractions.

BACKGROUND OF THE INVENTION

The presence of arsenic in its various chemical forms as an impurity in products or feed stocks can be detrimental to the use of such products or feed stocks. For example, the presence of arsenic in even small quantities is undesirable in industrial gases, hydrocarbon feed stocks, fuels, natural gases, etc. Also, the presence of arsenic in industrial effluent streams such as off-gases from refinery and gasification processes and the like may create health hazards and/or might be subject to environmental controls.

Most crude oils and shale oils contain arsenic in one form or another. When such oils are cracked, fractionated or otherwise treated to separate petroleum fractions, the resulting petroleum fractions will contain arsenic. When such petroleum fractions are to be subjected to combustion or further treatment, particularly when the treatment involves a catalyst comprising a noble metal, the presence of arsenic is harmful since it can poison the nobel metal catalyst. The presence of arsenic is particularly harmful in hydrocarbon fractions which are subjected to further processing in the presence of a catalyst comprising palladium or platinum. Various methods of removing arsenic impurities, especially arsine, from gaseous streams have been developed, but improved processes are still desired.

SUMMARY OF THE INVENTION

It is an object of this invention to provide an improved process for the removal of arsines (i.e., arsine and hydrocarbyl arsines) from gaseous streams of various chemical compositions, which contain also hydrogen sulfide. It is another object of this invention to provide a process for the removal of arsines from gaseous hydrocarbon streams, e.g., light paraffin and/or olefin streams, which also contain hydrogen sulfide. It is still another object of this invention to remove arsines from such hydrocarbon streams which are to be subjected to catalytic hydrogenation for removal of impurities such as small amounts of diolefins or acetylenes. A further object of this invention is to provide a process for the removal of arsines from gaseous streams of hydrocarbons, which also contain hydrogen sulfide, by contacting such streams with a mixed metal oxide sorbent. Other objects, advantages and features of the invention will be readily apparent to one skilled in the art from the following detailed description of the invention and the appended claims.

In accordance with the invention, arsines ($AsH_3$ and/or hydrocarbyl arsines) are removed from gaseous streams, which contain arsines and also hydrogen sulfide, by contacting such streams with a sorbent composition comprising (a) copper (II) oxide and (b) zinc oxide, under such conditions as will result in a gaseous stream having a reduced content of arsines. Preferably said sorbent composition has been prepared by a method comprising the steps of coprecipitating the hydroxides of copper and zinc and then calcining, i.e., heating in a non-reducing atmosphere, the formed hydroxides so as to substantially convert them to the oxides of copper and zinc. The CuO-ZnO sorbent composition is contacted with the gas streams in any suitable manner, preferably by passing the gas streams through fixed beds containing said sorbent composition under suitable reaction conditions. In one embodiment, an inert oxide, preferably alumina, is also present in the sorbent composition. Preferably, this sorbent composition has been prepared by a method comprising the steps of coprecipitating hydroxides of copper, zinc and aluminum and then calcining the hydroxides so as to substantially convert then to CuO, ZnO and $Al_2O_3$.

In a preferred embodiment, a gaseous stream of hydrocarbons, which contains arsines and hydrogen sulfide, is purified by contact with the sorbent composition of this invention under suitable reaction conditions. In another preferred embodiment, arsines are removed from such a hydrocarbon stream, which also contains hydrogen sulfide and which is to be further processed by contact with a nobel metal catalyst, so as to prevent poisoning of said noble metal by arsines. In still another preferred embodiment, an inert gas stream, which contains arsines and hydrogen sulfide, is contacted with said coprecipitated/calcined CuO-ZnO sorbent composition.

DETAILED DESCRIPTION OF THE INVENTION

In the process of this invention, at least a substantial portion of arsines (e.g., arsine ($AsH_3$) and hydrocarbyl arsines) is removed from gas streams also containing hydrogen sulfide. The arsines involved can be characterized by the formula $AsR_xH_{3-x}$, wherein R is a hydrocarbyl group having from 1 to 8 carbon atoms and x is 0, 1, 2 or 3. The hydrocarbyl groups can include any radical consisting of carbon and hydrogen, such as, alkyl, cycloalkyl and aryl groups. Since the exact state in which arsine impurities are present in various streams to be purified is not always known an may even vary during processing, such impurities will be referred to herein simply as "arsines," which will be understood to include arsine and hydrocarbyl arsines.

The present invention can be used to purify any suitable gaseous stream containing arsines and hydrogen sulfide. The invention is particularly effective in the purification of hydrocarbon streams including natural gas and gaseous petroleum fractions, comprising paraffins and/or olefins having from 1 to about 6 carbon atoms, such as methane, ethane, ethylene, propane, propylene, butane, hexane and the like. Frequently these hydrocarbon streams are to be subjected to further processing with catalysts comprising noble metals. In one embodiment, light petroleum fractions can be purified in accordance with this invention prior to their entry into a dehydrogenation process. Non-oxidative gases from coal gasification or natural gases can also be treated by the method of the present invention for removal of arsines. Various inert and combustible gases can be purified, including CO, $CO_2$, and inert gas selected from the group consisting of elements of Group O of the Periodic Table (He, Ne, Ar, Kr, Xn) and nitrogen.

The sorbent composition useful in this invention comprises (a) copper (II) oxide (CuO) and (b) zinc oxide (ZnO), preferably in coprecipitated form. The sorbent composition comprising CuO and ZnO can be used as such or in conjunction with a carrier, e.g., alumina, silica and other refractory oxides, preferably alumina. More preferably the CuO-ZnO-Al$_2$O$_3$ sorbent composition is prepared by coprecipitation. The sorbent compositions of this invention are commercially available and are marketed as catalysts for various reactions (but are not sold or advertised as sorbents), e.g., by United Catalysts, Inc. (formerly Girdler Chemical, Inc.), Louisville, Ky. under the product designation G-66A (CuO-ZnO-Al$_2$O$_3$) and G-66B (CuO-ZnO), and by BASF Wyandotte Corporation, Parsippany, NJ, under the product designation K-3-10 (CuO-ZnO-Al$_2$O$_3$). The sorbent compositions of this invention are preferably prepared by coprecipitation of hydroxides of copper, zinc and, optionally, aluminum from aqueous solutions containing salts of these metals (e.g., copper (II) nitrate, zinc nitrate and, optionally, aluminum nitrate) by addition of a basic substance (e.g., aqueous ammonia), and subsequent calcination in a non-reducing atmosphere (preferably in air) of the coprecipitated hydroxides so as to form the corresponding oxides. The use of the arsine sorbents prepared by impregnation of a carrier, e.g., alumina, with copper and zinc compounds (e.g., nitrates) and subsequent calcination is presently not preferred.

The weight ratio of CuO to ZnO generally ranges from about 20:1 to about 1:20, preferably from about 3:1 to about 1:3. When Al$_2$O$_3$ is present, the weight ratio of Al$_2$O$_3$ to (CuO plus ZnO) ranges from about 1:100 to about 10:1, preferably from about 1:5 to about 2:1. The surface area (determined by the BET/N$_2$ method) of the sorbent materials of this invention generally ranges from about 10 m$^2$/g to about 300 m$^2$/g, preferably from about 50 m$^2$/g to about 200 m$^2$/g. The pore volume (determined by mercury porosimetry at 15 Kpsi Hg) of the sorbent materials generally ranges from about 0.05 cc/g to about 1 cc/g, preferably from about 0.1 cc/g to about 0.5 cc/g. The sorbent materials can be used in powder form, or more conveniently, in agglomerated forms such as tablets or pellets or spheres.

It is believed that in the process of this invention, CuO reacts with arsines as well as with hydrogen sulfide present in the gas streams to be purified, whereas zinc oxide reacts primarily with H$_2$S. It is further believed that primarily arsenides and sulfides of copper and zinc sulfide are formed. It may be desirable to remove a portion of H$_2$S from the gas streams, e.g., by scrubbing with an alkaline solution, before the gas streams are contacted with the sorbent of this invention.

As arsine impurities contact, adhere to and react with the sorbent, the capacity of individual molecular units in the catalyst to retain such arsenic impurities is eventually reached and breakthrough occurs. In this context, the term "breakthrough" means the passage of undesirably large amounts of arsines beyond or downstream of the sorbent. Usually such breakthrough is considered to occur when the percentage of the arsenic not removed in relation to the arsenic content of the charged stock exceeds about 1%. In laboratory evaluations or in observations of industrial processes, the effectiveness of the sorbent can be evaluated by the number of hours during which a charged stock containing known concentrations of arsenic impurities can be passed over the sorbent prior to breakthrough occurring.

Once breakthrough occurs and the CuO-ZnO sorbent material is saturated with arsenic and/or sulfur compounds, the process can be continued by replacing the sorbent with fresh material by regenerating the spent sorbent, e.g., by heating it with a free oxygen containing gas (e.g., air) so as to convert the formed arsenic and sulfur compounds of copper and zinc back to their oxides, which are effective as sorbents for arsines and hydrogen sulfide.

Suitable sorbent compositions comprising CuO-ZnO can be designed to purify streams containing arsines and hydrogen sulfide in almost any concentration. However, this process is most effective in removing relatively small concentrations of impurities which are not amenable to removal by other chemical methods. Generally, the concentration of arsines in the streams to be purified is in the range of from about 10 ppb to about 200 ppm As, preferably in the range of about 10 ppb to 50 ppm As, measured on a mole basis, (i.e., 1 ppm means 1 mole of As as arsines per million moles of feed gas; 1 ppb means 1 mole of As as arsines per billion moles of feed gas). Generally, the concentration of hydrogen sulfide in the gas streams to be purified ranges from about 0.1 ppm to about 100 ppm, preferably from about 0.1 ppm to about 10 ppm, measured on a mole basis. The concentration of arsine impurities is preferably reduced to concentrations of less than about 10 ppb As.

The catalytic sorbents useful in the invention can be employed in various suitable combinations of process conditions, depending upon the nature of the streams to be purified and the further processing they are to undergo. Temperatures for contacting the stream with the sorbent can be in the range of from about 50° F. to about 500° F., preferably in the range of from about 70° F. to about 400° F. The invention can be carried out in ambient or elevated pressures in the range of from about 0 to about 3000 psig, preferably in the range of from about 10 to about 2000 psig. With gaseous streams, the stream to be purified can be passed over the catalytic sorbent at a gas hourly space velocity (GHSV) under standard conditions (i.e., at 0° C./1 atm) in the range of from about 100 to about 4000, preferably in the range of from about 600 to 2000, cc per cc sorbent per hour.

Treatment of the streams to be purified can be effected in any suitable manner. For example, in a preferred embodiment a bed of the catalytic sorbent is placed as a fixed bed in a confined zone, and a hydrocarbon fraction is passed therethrough in either upward or downward flow. Other suitable, yet less preferred methods of treatment can include a fluidized operation in which a hydrocarbon fraction and the catalytic sorbent particles are maintained in a state of turbulence under hindered settling conditions in a confined zone, moving bed operations in which the catalytic sorbent passes as a moving bed countercurrently to or concurrently with a gaseous petroleum fraction, etc. In a fixed bed operation for a continuous process, the flow of fluid can be rotated between two or more sorbent beds comprising CuO and ZnO with at least one being in regular operation, the other being in a regeneration mode. Continuous processes are preferred, but it is understood that batch type operations can be employed when desired.

The sorbent composition that contains arsenic and sulfur compounds is capable of being regenerated. Regeneration can be accomplished by conventional means, preferably by an oxidation step employing a free oxygen containing gas (e.g., air), whereby at least a portion of copper and zinc in said sorbent composition is converted to CuO and ZnO). Generally an elevated temperature is desirable during the oxidative operation, usually a temperature exceeding 50° F.

A further embodiment of this invention resides in a process for treating hydrocarbons containing arsine impurities, small amounts of H$_2$S and olefinic impurities. In accordance with this embodiment, this hydrocarbon feedstream is first contacted with the CuO-ZnO containing sorbent material disclosed above to form a substantially arsine- and H$_2$S-free intermediate stream. At least a portion of this stream is then contacted with a noble metal catalyst and hydrogen to convert a significant portion of the olefins by hydrogenating to saturated hydrocarbons. The preferred catalyst of this two-step process is one which comprises palladium and/or platinum metal on a solid carrier (support) material.

In yet another embodiment, the process of this invention comprises the use of the CuO-ZnO containing sorbent of this invention for the removal of arsine impurities from hydrocarbon streams containing also hydrogen sulfide and at least one of ethane and propane, which are to be thermally cracked to produce primarily ethylene, hydrogen, plus "pyrolysis gasoline". The presence of arsine impurities in these products is undesirable, since each of the products may subsequently come into contact with a catalyst easily poisoned by arsenic.

In still another embodiment, a process is provided comprising the use of the CuO-ZnO containing sorbent of this invention to remove arsine impurities from petroleum fractions comprising alkanes and hydrogen sulfide as impurities. The thus treated petroleum fractions are then subjected to dehydrogenation processes using noble metal catalyst such as platinum or palladium.

Yet another embodiment of the invention is a process comprising the treatment of mixtures of olefins, e.g. a stream from a catalytic oil cracker off-gas containing arsines and H$_2$S, with the sorbent composition of this invention for removal of arsines by the method of this invention. Such mixtures can contain olefins having from 2 to 6 carbon atoms.

Another embodiment is a process for treating a first stream comprising olefins having from 2 to about 6 carbon atoms and containing arsine impurities and hydrogen sulfide, said first stream being essentially free of acetylenes, comprising the step of contacting the first stream with the coprecipitated CuO-ZnO sorbent composition of this invention to substantially reduce the arsine content of the resulting treated first stream. The thus treated first stream can then be admixed with a second stream comprising olefins having from 2 to about 6 carbon atoms and containing acetylenic and/or diolefinic impurities, but being essentially free of arsines, and subsequently contacting at least a portion of the resulting admixture with hydrogen and a noble metal hydrogenation catalyst to selectively hydrogenate a substantial portion of the acetylenic and/or diolefinic impurities to olefins.

The process of this invention will be further illustrated by the following non-limiting examples.

EXAMPLE I

This example illustrates the removal of arsine (AsH$_3$) and H$_2$S from an ethylene-rich gas stream using a commercially available, coprecipitated CuO-ZnO catalyst material, Girdler GC-66C-RS, as the arsine/H$_2$S absorbent in accordance with the present invention. The 10/40 mesh sorbent material (GC-66C-RS, herein referred to as Sorbent A), provided by United Catalysts, Inc., Louisville, KY, comprised about 33 weight-% CuO and about 66 weight-% ZnO, and had a surface area of about 71 m$^2$/g (as determined by the BET/N$_2$ method). The sorbent material was oxidized at 380° C. for several hours before it was used.

A stainless steel tube reactor of 0.2 inch diameter and 20 inches length was wound with copper tubing for steam heating. The reactor was packed with a 10 inch bottom layer of glass beads, a 5 inch middle layer of the sorbent material and a 5 inch top layer of glass beads. The ethylene-containing feed gas stream from a commercial fluid bed catalytic cracking (FCC) unit contained about 10–25 ppb As as arsines plus H$_2$S (approximately 1 weight-%). This gas stream, from which hydrogen had been removed, was first passed through a tank containing a 5 weight-%, aqueous NaOH solution for removal of most H$_2$S, and was then downwardly passed through the reactor tube containing the oxidized CuO-ZnO sorbent material described earlier. The reactor temperature was about 95° C., and the gas feed rate was about 95 l/hr. The exiting gas stream was first allowed to bubble through two traps in series, each containing 5 cc of a solution of 0.25 weight percent silver diethyl dithiocarbamate in pyridine for detection of As, was then passed through a trap containing 10 weight percent aqueous HCl, and was finally vented.

After about 1 month on stream, no arsine breakthrough had occurred. The treated product gas contained less than 0.7 ppb As. The reactor was allowed to cool, and the CuO-ZnO sorbent layer was removed in four portions and analyzed. Results of this run (Run 1) are listed in Table I.

TABLE I

| CuO—ZnO Layer | Weight (grams) | Weight of S (grams) | Weight of As (grams) |
|---|---|---|---|
| First (Top) | 14.4 | 1.43 | 2.58 × 10$^{-3}$ |
| Second | 14.6 | 0.64 | 0.89 × 10$^{-3}$ |
| Third | 13.9 | 0.21 | 0.01 × 10$^{-3}$ |
| Fourth | 15.6 | 0.03 | ~0 |
| Total: | 58.5 | 2.31 | 3.48 × 10$^{-3}$ |

Data in Table I show that the CuO-ZnO absorbent removed essentially all arsine contained in the gas feed and also a substantial amount of H$_2$S.

EXAMPLE II

In this example the absorption of arsine from a nitrogen stream containing both arsine (500 ppm AsH$_3$) and hydrogen sulfide (0.125 volume-% H$_2$S) is described. The reactor used in this example was a glass tube of 6 mm diameter. Two absorbents were compared.

In invention run 2, 0.5 grams of BASF's commercial catalyst composition K-3-10 was employed. K-3-10 was prepared by coprecipitation and calcination. It contained 27.0 wt-% Cu as CuO, 13.0 wt-% Zn as ZnO, and Al$_2$O$_3$ as the balance. This material (herein referred to as Sorbent B) had a surface area of 125 m$^2$/g and a pore volume of 0.35 cc/g. It was supplied by BASF Wyandotte Corporation, Parsippany, NJ.

The second sorbent material (herein referred to as Sorbent C) was 0.5 grams of coprecipitated CuO/Al$_2$O$_3$. It was prepared by dissolving 66 grams of Al$_2$(SO$_4$)$_3$+14–16H$_2$O and 17.3 grams of CuSO$_4$+5H$_2$O in 300 mL of distilled water. A second solution containing 30 grams of NaOH dissolved in 100 mL of H$_2$O was slowly added to the first solution with stirring so as to coprecipitate Cu-Al hydroxides. The precipitate was washed three times by slurrying in water and filtering, dried at about 110° C. and calcined at about 500° C. for two hours (so as to convert the hydroxides to CuO- Al$_2$O$_3$). The calcined sorbent contained 28 weight-% Cu.

The gas feed stream (containing AsH$_3$ and H$_2$S) was passed through the reactor at a feed rate of about 0.13 ft$^3$/hr, a reaction temperature of about 70° F., and atmospheric pressure. In invention run 2 (with 0.5 g coprecipitated CuO-ZnO-Al$_2$O$_3$), arsine breakthrough occurred after 1.48 standard cubic feed (SCF) of the feed gas had passed through the reactor (during a period of about 6 hours). In control run 3 (with 0.5 g coprecipitated CuO-Al$_2$O$_3$), arsine breakthrough occurred after only 1.17 SCF of the feed gas had passed through the reactor (during a period of about 4.5 hours). Thus coprecipitated CuO-ZnO-Al$_2$O$_3$ containing 28 weight-% Cu had a 26% higher capacity for absorbing AsH$_3$ than coprecipitated CuO-Al$_2$O$_3$ also containing 28 weight-% Cu.

EXAMPLE III

In this example, the capacity for arsine absorption from a nitrogen stream, which contained 1038 ppm AsH$_3$ but did not contain H$_2$S, by invention Sorbent B and control Sorbent C is compared. The experimental conditions were essentially the same as those described in Example II. The weight of Sorbents B and C was 0.5 grams; the gas feed rate was 0.23-0.25 ft.$^3$/hr.; the reaction temperature was 70° F.; and the pressure was atmospheric. The total capacity for arsine absorption (at the time of arsine breakthrough) was 0.636 SCP for Sorbent B and 0.663 SCF for Sorbent C. These results indicate that the coprecipitated CuO-ZnO-Al$_2$O$_3$ was not superior to coprecipitated CuO-Al$_2$O$_3$ in terms of arsine absorption from a gas stream containing no H$_2$S. As was shown in Example II, the superiority of a CuO-ZnO sorbent versus a CuO sorbent is only realized when the feed gas contains an arsine plus H$_2$S as impurities.

EXAMPLE IV

In this example the arsine absorption effectiveness of coprecipitated versus impregnated CuO-containing sorbent materials is compared. Sorbent C (coprecipitated CuO-Al$_2$O$_3$ containing 28 weight-% Cu) was compared with Sorbent D (also containing 28 weight-% Cu), prepared by impregnation of alumina with a solution of Cu(NO$_3$)$_2$ in methanol, drying and calcination of 500° F. for 1 hour. A stream of N$_2$ containing 1038 ppm AsH$_3$ (no H$_2$S) was passed through the reactor (described in Example II) filled with 0.5 grams of either Sorbent C or Sorbent D, at a feed rate of 0.23-0.26 ft.$^3$/hr., at a reactor temperature of about 70° F., and atmospheric pressure. At the time of arsine breakthrough, coprecipitated CuO-Al$_2$O$_3$ (Sorbent C) had absorbed 0.663 SCF of arsine, whereas impregnated CuO-Al$_2$O$_3$ (Sorbent D) had absorbed only 0.155 SCF of arsine. Based on these results, it is believed that also coprecipitated CuO-ZnO-Al$_2$O$_3$ has a much higher capacity for arsine absorption than CuO-ZnO-Al$_2$O$_3$ prepared by impregnation, both having the same CuO content. Thus the use of CuO-ZnO or CuO-Zn-Al$_2$O$_3$ sorbent materials, which have been prepared by impregnation, for arsine removal from gas streams is less preferred.

EXAMPLE V

This example illustrates the regneration of a spent CuO-containing sorbent, which had absorbed the maximum amount of arsine it could absorb under conditions essentially the same as those described in Example II. The sorbent material (herein referred to as Sorbent E) was alumina impregnated with about 1 weight-% Cu (as CuO). 4 grams of this material had absorbed 0.248 SCF of arsine from the N$_2$/AsH$_3$ feed at about 74° F. before arsine breakthrough occurred.

Air was passed through the spent sorbent at a temperature of about 73° F. Then the air flow was stopped and a N$_2$/arsine feed stream was passed through the oxidized (regenerated) CuO-Al$_2$O$_3$ sorbent. At the time of arsine breakthrough, the regenerated sorbent material had absorbed 0.286 SCF of arsine, i.e., sightly more than the fresh sorbent material. Based on this data, it is believed that the sorbent material of this invention, namely copreciapted CuO-ZnO optionally containing Al$_2$O$_3$ or another inert refractory material, can also be regenerated by oxidation with an O$_2$-containing gas.

Reasonable variations and modifications are possible within the scope of the disclosure and appended claims.

We claim:

1. A process for removing arsine impurities from a gaseous stream comprising the step of (A) contacting said stream, which contains at least one arsine and also hydrogen sulfide, with a sorbent composition comprising (a) CuO and (b) ZnO, under such conditions as will result in a stream having a reduced content of arsine, wherein the weight ratio of CuO to ZnO in said sorbent composition is in the range of from about 20:1 to about 1:20.

2. A process in accordance with claim 1 wherein the sorbent composition has been prepared by a method comprising the steps of coprecipitating hydroxides of copper and zinc and then calcining the hydroxides so as to substantially convert them to CuO and ZnO.

3. A process in accordance with claim 1 wherein said sorbent composition further comprises aluminum oxide.

4. A process in accordance with claim 3 wherein the sorbent composition has been prepared by a method comprising the steps of coprecipitating hydroxides of copper, zinc and aluminum and then calcining the hydroxides so as to substantially convert them to CuO, ZnO and Al$_2$O$_3$.

5. A process in accordance with claim 2 wherein said gaseous stream is a hydrocarbon stream.

6. A process in accordance with claim 2 wherein said gaseous stream comprises gas selected from the group consisting of helium, neon, argon, krypton, xenon, nitrogen, carbon monoxide and carbon dioxide.

7. A process in accordance with claim 1 wherein said arsine has the formula AsR$_x$H$_{3-x}$, wherein each R is a hydrocarbyl group having from 1 to about 8 carbon atoms and x is either 0, 1, 2 or 3.

8. A process in accordance with claim 7 wherein at least a portion of said arsenic is present as AsH$_3$.

9. A process in accordance with claim 1 wherein said weight ratio of CuO to ZnO is in the range of from about 3:1 to about 1:3.

10. A process in accordance with claim 4 wherein the weight ratio of Al$_2$O$_3$ to (CuO plus ZnO) in the sorbent composition ranges from about 1:100 to about 10:1.

11. A process in accordance with claim 10 wherein said weight ratio of Al$_2$O$_3$ to (CuO plus ZnO) ranges from about 2:1 to about 1:5.

12. A process in accordance with claim 2 wherein said sorbent composition has a surface area in the range of from about 10 to about 300 m$^2$ per gram and a pore volume in the range of from about 0.05 about to 1.0 cc per gram.

13. A process in accordance with claim 2 wherein said conditions comprise a temperature ranging from about 50° to about 500° F., a pressure ranging from 0 to about 3,000 psig, and a gas hourly space velocity ranging from about 100 to about 4,000 cc/cc sorbent/hr.

14. A process in accordance with claim 13 wherein the temperature is in the range of from about 70° to about 400° F., the pressure is in the range of from about 10 to about 2000 psig and the gas hourly space velocity is in the range of from 600 to about 2000 cc/cc sorbent/hr.

15. A process in accordance with claim 1 comprising the additional step of (B) passing a free oxygen containing gas over the sorbent composition that has been contacted with gaseous stream in step (A), under such conditions as to convert at least a portion of compounds of copper and zinc in said sorbent composition to CuO and ZnO.

16. A process in accordance with claim 2 comprising the additional step of (B) passing a free oxygen containing gas over the sorbent composition that has been contacted with said gaseous stream in step (A), under such conditions so as to convert at least a portion of compounds of copper and zinc in said sorbent composition to CuO and ZnO.

17. A process in accordance with claim 4 comprising the additional step of (B) passing a free oxygen containing gas over the sorbent composition that has been contacted with said gaseous stream in step (A), under such conditions so as to convert at least a portion of compounds of copper and zinc in said sorbent composition to CuO and ZnO.

18. A process for treating an olefin containing feed stream comprising the steps of
(A) contacting the olefin containing hydrocarbon feed stream, which also contains arsine and $H_2S$, with a sorbent material comprising (a) CuO and (b) ZnO, under such conditions as will result in an intermediate hydrocarbon stream having a reduced arsine content, wherein the sorbent composition has been prepared by a method comprising the steps of coprecipitating hydroxides of copper and zinc and then calcining the hydroxides so as to substantially convert them to CuO and ZnO and wherein the weight ratio of CuO to ZnO in said sorbent composition is in the range of from about 20:1 to about 1:20; and
(B) contacting at least a portion of said intermediate hydrocarbon stream with hydrogen and a noble metal hydrogenation catalyst at hydrogenation conditions so as to substantially hydrogenate said olefins present in said intermediate stream.

19. A process in accordance with claim 18 wherein said noble metal catalyst comprises at least one metal selected from the group consisting of palladium and platinum on a solid support.

20. A process in accordance with claim 18, wherein the sorbent composition further comprises (c) $Al_2O_3$ and has been prepared by a method comprising the steps of coprecipitating hydroxides of copper, zinc and aluminum and then calcining the hydroxides so as to substantially convert them to CuO, ZnO and $Al_2O_3$.

21. A process in accordance with claim 18, wherein said sorbent composition further comprises (c) $Al_2O$ and has been prepared by a method comprising the steps of coprecipitating hydroxides of copper, zinc and aluminum and then calcining the hydroxides so as to substantially convert them to CuO, ZnO and $Al_2O_3$ and wherein said noble metal catalyst comprises at least one metal selected from the group consisting of palladium and platinum on a solid support.

22. A process comprising the steps of
(A) contacting a first gaseous stream comprising olefins having from 2 to 6 carbon atoms, arsines and hydrogen sulfide, being essentially free of acetylenes, with a sorbent composition comprising CuO and ZnO under such conditions as will result in a first treated gas stream having a reduced arsine content, wherein the weight ratio of CuO to ZnO in said sorbent composition is in the range of from about 20:1 to about 1:2;
(B) admixing said first treated gas stream with a second gas stream comprising olefins having from 2 to 6 carbon atoms and also acetylenic impurities, said second stream being essentially free of arsines; and
(C) contacting at least a portion of said admixture of first treated gas stream and second gas stream with hydrogen and a noble metal hydrogenation catalyst at hydrogenation conditions so as to selectively hydrogenate a substantial portion of said acetylenic impurities to olefins.

23. A process in accordance with claim 22 comprising the additional steps of
(D) passing a free oxygen containing gas over the sorbent composition that has been contacted with said gaseous stream in step (A), under such conditions as to convert at least a portion of compounds of copper and zinc in said sorbent composition to CuO and ZnO.

24. A process in accordance with claim 22, wherein the sorbent composition has been prepared by a method comprising the steps of coprecipitating hydroxides of copper and zinc and then calcining the hydroxides so as to substantially convert them to CuO and ZnO.

25. A process in accordance with claim 22, wherein the sorbent composition further comprises (c) $Al_2O_3$ and has been prepared by a method comprising the steps of coprecipitating hydroxides of copper, zinc and aluminum and then calcining the hydroxides so as to substantially convert them to CuO, ZnO and $Al_2O_3$.

* * * * *